US009216075B2

United States Patent
Bailly et al.

(10) Patent No.: US 9,216,075 B2
(45) Date of Patent: Dec. 22, 2015

(54) ELEMENT FOR REINFORCING A MESH

(75) Inventors: Pierre Bailly, Caluire (FR); Geneviève Doucet, Villefranche sur Saone (FR)

(73) Assignee: Sofradim Production (FR)

( * ) Notice: Subject to any disclaimer, the term of this patent is extended or adjusted under 35 U.S.C. 154(b) by 787 days.

(21) Appl. No.: 13/500,985

(22) PCT Filed: Oct. 8, 2010

(86) PCT No.: PCT/EP2010/065131
§ 371 (c)(1),
(2), (4) Date: May 14, 2012

(87) PCT Pub. No.: WO2011/042553
PCT Pub. Date: Apr. 14, 2011

(65) Prior Publication Data
US 2013/0060263 A1    Mar. 7, 2013

(30) Foreign Application Priority Data
Oct. 9, 2009    (FR) ...................................... 09 57061

(51) Int. Cl.
*A61B 17/08*    (2006.01)
*A61F 2/00*    (2006.01)

(52) U.S. Cl.
CPC .................................. *A61F 2/0063* (2013.01)

(58) Field of Classification Search
CPC . A61F 2/0063; A61F 2002/0068; A61F 2/00; A61F 2/0004; A61F 2002/0072; A61F 2002/016; A61F 6/22; A61F 6/225; A61F 2250/0006; A61F 2250/001; A61B 17/0057; A61B 17/00597; A61B 17/12031; A61B 17/12122; A61B 2017/00584; A61B 2017/00592; A61B 2017/00606; A61B 2017/00615; A61B 2017/00641

USPC .......................................................... 606/151
See application file for complete search history.

(56) References Cited

U.S. PATENT DOCUMENTS 6,712,836 B1 * 3/2004 Berg et al. ...................... 606/213
2003/0158604 A1 8/2003 Cauthen et al.
(Continued)

FOREIGN PATENT DOCUMENTS

EP    0 544 485 A1    6/1993
EP    1 138 277 A1    10/2001
(Continued)

OTHER PUBLICATIONS

International Search Report for Appln. No. PCT/EP2010/065131 mailed Nov. 12, 2010.

*Primary Examiner* — David C Eastwood
*Assistant Examiner* — Martin T Ton

(57) ABSTRACT

The present invention relates to a reinforcing element (200) for a circular mesh, comprising a plurality of fingers (201) which, at rest, form a conical structure (202) that can open out when the reinforcing element is placed under axial stress, each finger comprising a vertex segment (201*a*) and a peripheral segment (201*b*) defining a vertex part (202*a*) and a peripheral part (202*b*) of the said conical structure, the said reinforcing element comprising, for each finger, means (201*c*, 205; 402; 502) of misaligning the said vertex segment and the said peripheral segment, at least when the said reinforcing element is under axial stress, the said misalignment means making it possible, in the said position under axial stress, firstly for the peripheral part of the said conical structure to adopt a planar configuration, and secondly, for the said vertex part of the said structure to maintain a conical shape. The invention also relates to a prosthesis (300) comprising such a reinforcing element (200) associated with a mesh (1).

16 Claims, 7 Drawing Sheets

(56) References Cited

U.S. PATENT DOCUMENTS

2008/0045778 A1 2/2008 Lichtenstein et al.
2009/0076528 A1* 3/2009 Sgro ............................ 606/151
2009/0192530 A1 7/2009 Adzich et al.

FOREIGN PATENT DOCUMENTS

| GB | 2 397 240 A | 7/2004 |
| WO | 01/80773 A1 | 11/2001 |

* cited by examiner

ELEMENT FOR REINFORCING A MESH

CROSS-REFERENCE TO RELATED APPLICATIONS

This application is a U.S. National Stage Application filed under 35 U.S.C. §371(a) of International Application No. PCT/EP2010/065131, filed Oct. 8, 2010, which claims the benefit of and priority to French Application 09/57061 filed Oct. 9, 2009, the entire contents of which are incorporated by reference herein.

The subject of the present invention is a reinforcing element for reinforcing a mesh, for example intended to plug hernias, and a prosthesis comprising such a reinforcing element and a mesh.

In humans, the abdominal wall consists of fat and muscle interconnected by fascias. Sometimes, a break in continuity occurs in the fascias, allowing part of the peritoneum to slip through and form a sac, or hernia, containing either fat or part of the intestines. Hernias or incisional hernias (which are hernias that occur on a parietal surgical scar) present in the form of a bulge at the surface of the skin and are termed either umbilical or inguinal hernias or incisional hernias according to where they are located.

To repair a hernia problem, surgeons frequently resort to the placement of a prosthesis made of synthetic mesh which replaces or strengthens the weakened anatomical tissue.

However, such a prosthesis, once implanted, is subjected to abdominal pressure which tends to expel it outwards. Such pressure may cause reversion of the prosthesis and lead to risks of the hernia recurring.

Thus, the effectiveness of the prosthesis, and therefore the ability to minimise the risks of relapse, are to a large extent dependent on the good fixation of this prosthesis. In particular, before being fixed, the prosthesis has to be correctly spread out against the abdominal wall that it is intended to strengthen. Specifically, prostheses of the mesh type, that is to say based on an arrangement of filaments forming a textile, are generally flexible. In order to introduce them into the hernia opening, they are often folded on themselves to reduce their volume. They therefore have a tendency to form creases on the abdominal wall when introduced to the implantation site. Spreading them out in this respect is of key importance but may prove difficult, particularly when treating an umbilical hernia which, being smaller in size than an inguinal hernia, offers the surgeon very little work space in which to manipulate the prosthesis.

For example, in the case of umbilical hernias, or when seeking to repair trocar openings, or else as a preventive measure, the size of the problem being treated is small, measuring for example from 1 to 3 cm in diameter, and it is conceivable to perform open surgery. However, in this type of surgery, the surgeon has very little working space and very little visibility. He therefore preferably needs to have available a prosthesis that is easy to position, to spread out and to fix, if possible avoiding having to suture the periphery of the prosthesis, which is an operation which under such working conditions is complicated and difficult.

The specific problem is that if the prosthesis is not perfectly spread out against the abdominal wall there will be a risk of catching on the peritoneal sac and a risk of a soft organ becoming trapped between the prosthesis and the abdominal wall, with the potential to lead to risks of adhesion, pain and intestinal occlusion and to increase the possibility of the problem recurring. It is therefore essential for the surgeon to make sure that no part of the prosthesis is folded and that no viscera or part of the intestine has become trapped between the prosthesis and the abdominal wall. What is more, incorrect positioning of the sutures or poor fixation of the prosthesis carries the risk of distorting this prosthesis and of creating tension.

Thus, particularly in the case of an umbilical hernia in which the prosthesis introduction orifice is small in size, it would be advantageous to have available a prosthesis that was able, under stress, to occupy a small volume so that it could be introduced more easily into the abdominal cavity through the said opening, and which could then be deployed, spread out and flattened easily against the abdominal wall, even automatically without requiring significant handling of the prosthesis on the part of the surgeon.

Various prosthesis that can be folded on themselves and then deployed already exist.

For example, document WO-A-00/07520 discloses a prosthesis consisting of a flexible mesh reinforced by a double hoop provided with spokes. A filament slipped around a periphery of the larger hoop allows the prosthesis to be shaped into a cone frustum as it is introduced into the inguinal opening. However, spreading the prosthesis out and flattening it against the abdominal wall once it has been introduced to the implantation site require significant intervention on the part of the surgeon and are somewhat unsatisfactory. In addition, no means is provided for avoiding the risk of reversion of the prosthesis, once this prosthesis has been implanted and has become subjected to the abdominal pressure which tends to expel it outwards.

Document FR 2 810 536 describes a prosthesis based on a substantially circular mesh itself fitted with rolls of mesh allowing the prosthesis to adopt a cylindrical shape as it is being introduced at the implantation site. However, the spreading-out of this prosthesis is somewhat uncertain. Furthermore, such a prosthesis may carry a risk of reversion, once implanted and subjected to the abdominal pressure which tends to expel it outwards.

Document FR 2 769 825 describes a prosthesis of the mesh type of circular overall shape, equipped with radial reinforcing elements. However, such a prosthesis is not very well rigidified once implanted and may carry a risk of reversion when subjected to the abdominal pressure which tends to expel it outwards.

Document EP 0 544 485 describes a prosthesis of the mesh type of circular overall shape, equipped with radial reinforcing elements. However, no means is provided for preventing the risks of prosthesis reversion once this prosthesis has been implanted and subjected to the abdominal pressure which tends to expel it outwards.

The present invention relates to a reinforcing element intended to be associated with a mesh in order to form a prosthesis, which makes it possible on the one hand to reduce the volume occupied by the said prosthesis to allow it to be introduced easily through a small-sized incision and, on the other hand, to facilitate the spreading and fixation of the said prosthesis while at the same time avoiding the risks of reversion of the prosthesis when, once implanted, it is subjected to the abdominal pressure which tends to expel it outwards.

The present invention also relates to a prosthesis comprising such a reinforcing element and a mesh, particularly for treating hernias in the abdominal wall.

A first aspect of the present invention relates to an implantable reinforcing element, intended to be associated with a mesh, comprising a plurality of fingers extending from a single point and forming, when the said reinforcing element is in a rest configuration, a substantially conical structure in which the said single point is the vertex, the collection of the free ends of the said fingers forming the base of the said conical structure, the said fingers being fixed freely to the said vertex so as to allow the said conical structure to open out when the reinforcing element is placed under axial stress, in which the base of the said conical structure is brought into contact with a substantially planar surface and a pressure force is applied to the said reinforcing element from the vertex of the said conical structure towards the said base, each finger comprising a vertex segment and a peripheral segment, the collection of the said vertex segments of the said fingers defining a vertex part of the said conical structure and the collection of the said peripheral segments of the said fingers defining a peripheral part of the said conical structure, the said reinforcing element comprising, for each finger, means of misalignment the said vertex segment and the said peripheral segment, at least in the position in which the said reinforcing element is under axial stress, the said misaligning means making it possible, in the said position under axial stress, firstly, for the peripheral part of the said conical structure to adopt a substantially planar configuration and to hug the said substantially planar surface, and secondly for the said vertex part of the said structure to maintain a substantially conical shape.

What is meant within the meaning of the present application by "conical structure" or "substantially conical structure" is a structure that has the overall shape of a cone, it being possible for the cone to exhibit symmetry of revolution, to be pyramid-shaped or any other form of cone. For example, a structure in the shape of a sugarloaf is also included as being a substantially conical structure within the meaning of the invention.

What is meant within the meaning of the present application by "implantable reinforcing element" is a reinforcing element made of materials that are biocompatible and that can be introduced and implanted into the human body.

Because of its structure, the reinforcing element according to the invention has a certain degree of elasticity that allows it to deform under the effect of certain particular stresses and to revert to its rest configuration once these stresses have been relaxed.

As will become apparent from the description that follows, the reinforcing element according to the invention is able to rigidify a mesh that can be used for the manufacture of a prosthesis, particularly for treating hernias, and it can be used to shape this mesh in such a way that, under the effect of a stress, such as the abdominal pressure for example, the said mesh prevents any reversion of the prosthesis. Specifically, the reinforcing element according to the invention allows the prosthesis to be kept pressed firmly against the abdominal wall avoiding any prosthesis reversion. Once the prosthesis is implanted, the abdominal pressure naturally, and therefore automatically, places the reinforcing element under the axial stress as defined hereinabove, the said substantially planar surface being the abdominal wall.

In one embodiment of the invention, at least part of the said misalignment means is situated at the junction between the vertex segment and the peripheral segment. Thus, the misalignment of the vertex and peripheral segments comes about under the axial stress as defined hereinabove, which corresponds to the abdominal pressure when the reinforcing element is implanted in a prosthesis the mesh of which it reinforces.

In one embodiment of the invention, the said reinforcing element is able to adopt a substantially cylindrical configuration under radial and centripetal stress, in which configuration pressure is applied to the said peripheral segments in the radial and centripetal direction. Thus, it is possible to reduce the volume occupied by the prosthesis associated with the said reinforcing element, particularly at the time of introduction of this prosthesis through the hernia incision.

In one embodiment of the invention, each peripheral segment has a shape that widens towards the free end of the said finger. Such an embodiment allows the mesh to be spread out correctly once the reinforcing element is fixed to the mesh.

For example, at least one peripheral segment is perforated. In one embodiment of the invention, all the peripheral segments are perforated. Such an embodiment minimizes the amount of foreign body introduced into the patient while at the same time maintaining correct spreading-out of the mesh once it has been fixed to the reinforcing element.

In one embodiment of the invention, for each finger, the said vertex segment and the said peripheral segment are joined together and consist of a single elastic tab. Such an embodiment allows for simple manufacture of the reinforcing element which can thus be obtained as a single piece, using injection moulding.

A hole may then be provided in the said elastic tab at the junction between the vertex segment and the peripheral segment, a tie linking each finger to the adjacent finger by passing through the said holes, the said tie being tension-free when the said reinforcing element is in the rest position, the said tie being under tension in the position in which the said reinforcing element is under axial stress.

In another embodiment, the reinforcing element further comprises a plurality of flexible bridges of material, each bridge of material connecting a finger to an adjacent finger at the respective junctions between the vertex segments and peripheral segments of the said fingers, the said bridges of material being tension-free when the said reinforcing element is in the rest position, the said bridges of material being under tension when the said reinforcing element is in the position under axial stress.

As will become apparent from the description which follows, the tie or the bridges of material under tension prevent, when the reinforcing element is under axial stress, the fingers or elastic tabs from separating at the vertex part of the conical structure, making the latter impossible to compress such that it retains its conical shape, thus preventing any risk of reversion of the reinforcing element and therefore of the prosthesis.

Alternatively, the vertex segment and the peripheral segment may be slightly misaligned when the said reinforcing element is in the rest position.

For example, in such an embodiment, the said vertex segments define a conical sugarloaf shape of the said vertex part of the conical structure, the said peripheral segments defining an axisymmetric cone frustum. Thus, under axial stress, the pressure applied to the vertex of the sugarloaf causes the peripheral segments to flex as a result of the elasticity of the flexible tab; however, the vertex segments, because of their slightly rounded shape which gives the vertex part its sugarloaf shape, remain substantially in their initial position. The vertex part of the conical structure is therefore not compressible.

In one embodiment of the invention, the said misalignment means comprise a material deficiency created on the internal surface of the said conical structure, at the junction between the vertex segment and the peripheral segment of each finger. Thus, when, under axial stress, pressure is applied to the vertex of the conical structure of the reinforcing element, each finger bends at its part that has been weakened by the deficiency of material, misaligning the vertex segment with respect to the peripheral segment.

In one embodiment of the invention, a non-stick film is fixed to the external surface of the said conical structure of the reinforcing element, particularly so as to avoid the formation of undesired post-surgery severe fibrous adhesions.

What is meant within the meaning of the present application by "non-stick" is a smooth and non-porous biocompatible material or coating that does not offer space for cell regrowth.

In one embodiment of the invention, a centering filament is fixed to the vertex of the said conical structure. Alternatively, several centering filaments may be fixed to the reinforcing element. In other embodiments, the centering filament or filaments may be replaced by textile tapes. This or these centering filament(s) or tape(s) may for example be of use to the surgeon to make it easier to position the prosthesis equipped with the reinforcing element according to the invention at the center of the defect being treated and to close in the edges of the defect so that they can be sutured.

The present invention also relates to a prosthesis comprising an implantable mesh, characterized in that a reinforcing element as described hereinabove is fixed to the said mesh, the vertex of the said conical structure being positioned at the centre of the said mesh and the said mesh substantially hugging the surface of the said conical structure.

What is meant within the meaning of the present application by "mesh" is an arrangement of biocompatible filaments, such as a knit, a woven, a non-woven, preferably of open-cell (perforated) construction, that is to say one that has pores that encourage tissue regrowth. Such a mesh may be bioresorbable, permanent or partially bioresorbable. It is generally flexible enough that it can be folded onto itself at the time of introduction into the abdominal cavity. The mesh may be produced of one layer of textile or of several layers. Such meshes are well known to those skilled in the art. The mesh that can be used with the reinforcing element according to the invention may come in any form whatsoever, rectangular, square, circular, oval, etc., and then be cut to suit the shape of the hernia defect. For example, the mesh may be of circular or else oval overall shape; in such instances, the reinforcing element according to the invention preferably has a structure in the form of an axisymmetric cone or any other cone. Alternatively, the mesh may be of square or else rectangular overall shape, and in that case the reinforcing element according to the invention preferably has a structure in the form of a pyramid-shaped cone.

In one embodiment of the invention, the edges of the said mesh adjoin the free ends of the fingers of the said reinforcing element. As will become apparent from the description which follows, such an embodiment allows the prosthesis to be spread out correctly and allows it to be pressed more firmly against the abdominal wall. Such an embodiment also makes it possible to prevent the risks of viscera becoming trapped between the prosthesis and the abdominal wall.

In one embodiment of the invention, the prosthesis is covered on its external surface with a non-stick coating.

The present invention will become more clearly apparent from the following description and from the attached drawings in which.

Figure 1:
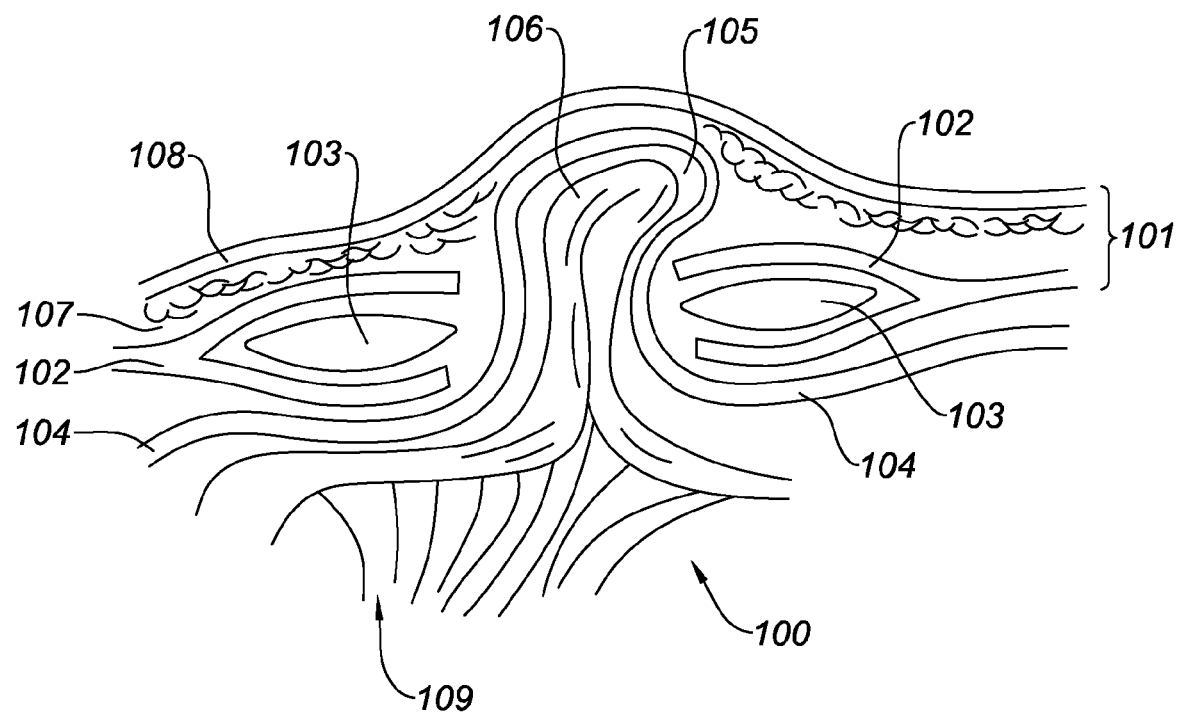
FIG. 1 is a cross section through a median abdominal hernia or incisional hernia.

FIG. 1 depicts a hernia 100 in the abdominal wall 101 which is characterized by a break in continuity of the fascia 102 surrounding the rectus muscles 103 and a protrusion of the peritoneum 104 forming a sac, the hernia sac 105, which contains either fat (epiploon) or part of the viscera 106, and which therefore presses on the fatty tissue 107 and lies flush with the skin 108. A hernia 100 operation involves repositioning the viscera 106 in the abdominal cavity 109 and keeping them there.

Figure 2:
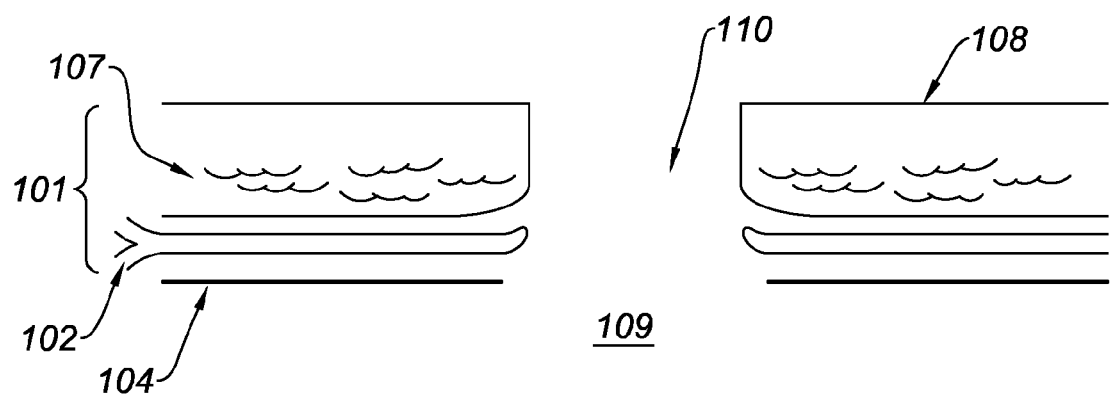
FIG. 2 is a simplified view of the hernia of FIG. 1 once the surgeon has made an abdominal incision.

FIG. 2 depicts the hernia 100 of FIG. 1 once the surgeon has made an incision in the skin 108, the abdominal wall 101 and the peritoneum 104 in order to reduce the hernia sac 105. The viscera have not been depicted in FIG. 2 as these have been pushed back into the abdominal cavity 109. The surgeon has now to introduce into the abdominal cavity 109, via the incision 110 that he has made, a prosthesis the purpose of which is to strengthen the abdominal wall, before closing the incision 110 using sutures for example. In the case of an umbilical hernia, the size of the incision 110 is particularly small, for example of the order of 1 to 3 cm in diameter.

Figure 3:
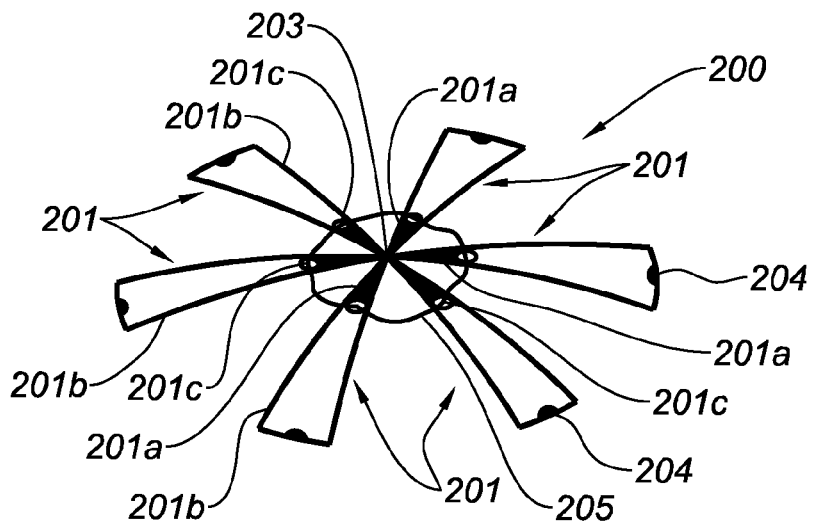
FIG. 3 is a perspective view of a first embodiment of the reinforcing element of the invention, at rest.
Figure 4:
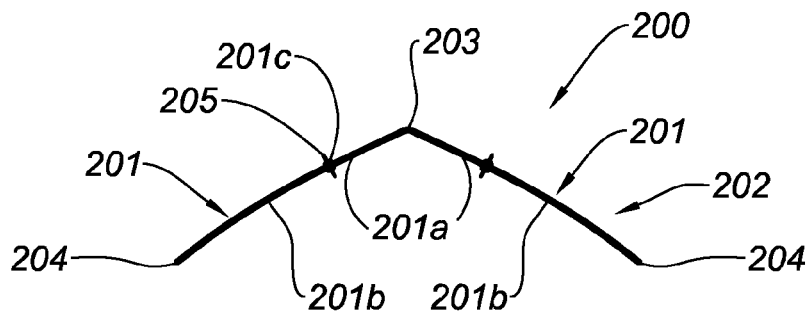
FIG. 4 is a cross section through the reinforcing element of FIG. 3.
Figure 5:
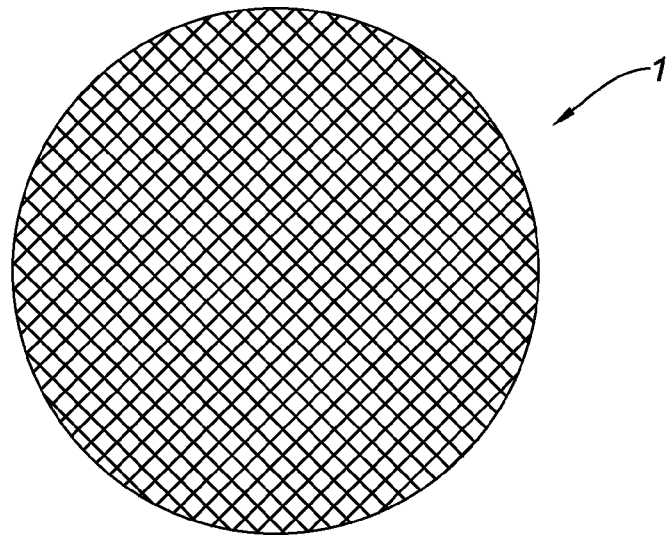
FIG. 5 is a view from above of a mesh that can be used with the reinforcing element of FIG. 3.

FIGS. 3 and 4 depict, in perspective and in section respectively, a first embodiment of a reinforcing element 200 according to the invention intended to be associated with an implantable mesh 1 of circular shape, as depicted in FIG. 5.

The mesh 1 is made of an arrangement of biocompatible filaments, such as a knit, a woven or a nonwoven. It may be bioresorbable, permanent or partially bioresorbable. In general, the mesh is of open cell construction and contains pores for better tissue integration. This mesh 1 is generally flexible enough that it can be folded over onto itself at the time of introduction into the abdominal cavity 109 via the incision 110. The mesh 1 may be made of one layer of textile or of several layers. The textile may be a two-dimensional or three-dimensional knit. Such meshes are well known to those skilled in the art and are not described in further detail here. The mesh may come in the form of a strip which is cut to the dimensions of the problem being treated. In the example depicted, the mesh 1 is of circular shape, tailored to the shape of the incision 110 for the hernia problem 100. In other embodiments, the shape of the mesh could be oval. Alternatively, the mesh may have a rectangular or square shape and in that case the conical structure of the reinforcing element may be in the shape of a pyramid cone.

The reinforcing element 200 is depicted in FIGS. 3 and 4 in a position at rest, with no stress applied to the said reinforcing element 200. The reinforcing element 200 comprises a plurality of fingers 201, six fingers 201 evenly spaced in the example depicted, extending from a single point and forming a substantially conical structure 202 the single point of which is the vertex 203. In other embodiments, the reinforcing element may comprise a different number of fingers, for example from 3 to 12 fingers. For example, in the case of a conical structure in the shape of a pyramid cone, the reinforcing element may comprise four fingers, each finger being situated at one corner of the pyramid.

With reference to FIGS. 3 and 4, each finger 201 comprises a free end 204, at the opposite end to its end that is fixed to the said vertex 203. The collection of the free ends 204 of the six fingers 201 forms the base of the conical structure 202. In the example depicted, the six fingers 201 have substantially the same length and the base of the conical structure 202 is substantially contained in a plane.

In other embodiments, the structure formed by the fingers of the reinforcing element may be a cone with a non-planar base. Likewise, the cone formed may be axisymmetric, pyramid-shaped or any other cone. Alternatively, as will become apparent from FIGS. 18a and 18b, part of the conical structure may be sugarloaf-shaped.

As will become apparent from FIGS. 6 and 7, the fingers 201 are fixed to the vertex 203 freely so as to allow the said conical structure 202 to open out when the reinforcing element 200 is placed under a certain stress, known as the axial stress and explained later on.

With reference to FIG. 3, each finger 201 has an elongate overall shape and is formed of two parts or segments joined together and substantially aligned with one another in the example depicted, these being a vertex segment 201a, starting from the vertex 203 and extending, in the example depicted, along approximately one third of the total length of the finger 201, and a peripheral segment 201b, extending over the remaining two-thirds of the length of the finger 201 as far as the free end 204 of the finger 201.

Thus, the collection of the vertex segments of the said fingers 201 defines a vertex part of the conical structure 202 and the collection of the peripheral segments of the said fingers 201 defines a peripheral part of the conical structure 202. As seen in FIGS. 3 and 4 in which the reinforcing element 200 is in its position of rest, the vertex part and the peripheral part of the conical structure 202 are substantially aligned with one another and substantially form an axisymmetric cone.

In the example depicted, for each finger 201, the vertex segment 201a has the form of a solid rod while the peripheral segment 201b has a shape that widens towards the free end of the finger 201, like a perforated palm in the example depicted: thus, the contours of the free ends 204 of the fingers 201 are present over a significant portion of the periphery of the base of the conical structure 202, while at the same time requiring a minimal quantity of material. As will become apparent later on in the description, the shape of the peripheral segments makes it possible to achieve optimum deployment and optimum pressing of the mesh intended to be reinforced by the reinforcing element 200, while at the same time minimizing the amount of foreign body present in the patient.

In the example depicted, for each finger 201, the vertex segment 201a and the peripheral segment 201b are joined together and consist of a single elastic tab.

The reinforcing element 200 may be made of any biocompatible material, whether or not this material is bioresorbable. In a preferred embodiment, it is made of a material that is bioresorbable. In this application, "bioresorbable" means the characteristic whereby a material is absorbed by the biological tissues and disappears in vivo after a given period of time which may, for example, vary from one day to several months according to the chemical nature of the material.

Thus, by way of bioresorbable materials suitable for the manufacture of the reinforcing element according to the present invention, mention may be made of polylactic acid (PLA), polycaprolactones (PCL), polydioxanones (PDO), trimethylene carbonates (TMC), polyvinyl alcohol (PVA), polyhydroxyalkanoates (PHA), oxidized cellulose, polyglycol acid (PGA), copolymers of these materials and mixtures thereof.

By way of non-bioresorbable materials suited to the production of the reinforcing element of the present invention, mention may be made of polypropylenes, polyesters such as polyethylene terephthalate, polyamides, polyetheretherketones (PEEK), polyaryletheretherketones (PAEK) and mixtures thereof.

The reinforcing element according to the invention may, for example, be produced as a single piece, by injection moulding one or more biocompatible thermoplastics. Alternatively, the reinforcing element according to the invention may also be obtained by cutting a sheet of material.

Because its construction is based on a plurality of fingers, the conical structure 202 is perforated and flexible. The reinforcing element thus has a certain degree of elasticity allowing it to deform under the effect of certain particular stresses which will be described hereinafter.

Moreover, at the junction between the vertex segment 201a and the peripheral segment 201b, there is an opening 201c, through which a tie 205 common to all six fingers 201 passes. This tie may, for example, be a filament, braided or otherwise, or alternatively a cord, made of biocompatible material. The tie 205 passes through the opening 201c in each finger 201 and forms a flexible ring. When the reinforcing element 200 is in the rest position as depicted in FIG. 3, this tie 205 is tension-free between the fingers 201 and is slightly slack between each finger.

Figure 6:
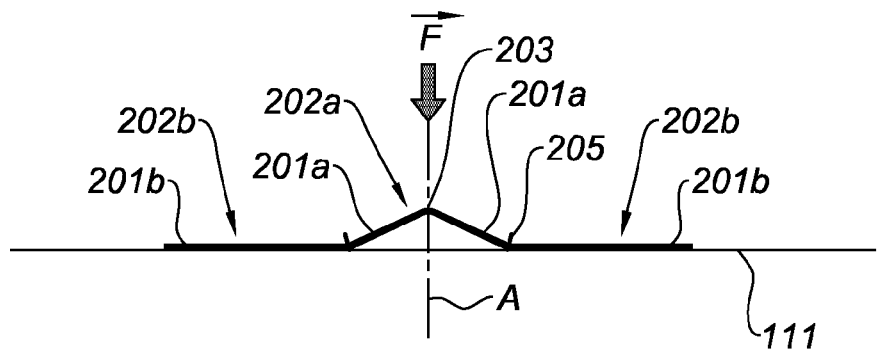
FIG. 6 is a cross section through the reinforcing element of FIGS. 3 and 4, under axial stress.
Figure 7:
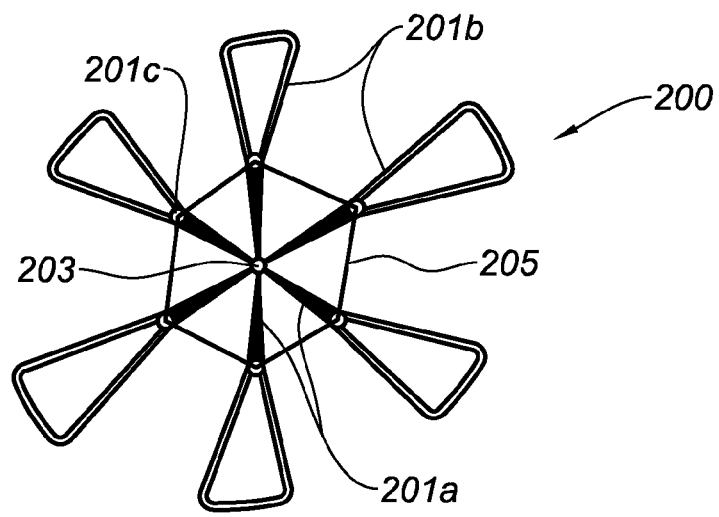
FIG. 7 is a view from above of the reinforcing element of FIGS. 3 and 4, under axial stress.

The conical structure 202 can thus open out under the effect of a stress known as an axial stress: one example of this situation that leads to this axial stress is illustrated in FIG. 6: in this illustrating situation, the base of the said conical structure 202 is brought into contact with a substantially planar surface 111, and a pressure force is applied to the said reinforcing element 200 from the vertex 203 of the said conical structure 202 towards the said base, the pressure force being embodied by the arrow F. Under this axial stress, each finger 201 has a tendency to separate from the central axis A of the conical structure 202 that passes through the vertex 203. However, under the effect of this stress and of the radial separation of the fingers 201 thus caused, the tie 205 between each of the fingers 201 becomes taut and prevents the vertex segments of the fingers 201 from separating any further in the radial direction. As application of the abovementioned pressure force continues, each finger 201 is caused to flex, particularly because the finger consists of an elastic tab, at the junction 201c between its vertex segment 201 and its peripheral segment 201b. The peripheral segments 201b of the fingers 201 spread out and hug the planar surface 111 with which the reinforcing element 200 has been brought into contact, as illustrated in FIG. 6. Thus, as is clearly visible in FIG. 6, under the axial stress as described hereinabove, the peripheral part 202b of the conical structure 202 adopts a substantially planar configuration and the vertex part 202a of the conical structure maintains a substantially conical shape. The vertex part 202a cannot be compressed. As is clear from this figure, for each finger 201, the peripheral segment 201b is no longer aligned with the vertex segment 201a. Likewise, the peripheral part 202b of the conical structure 202 is no longer aligned with the vertex part 202a of the conical structure 202. The tie 205 has thus acted as a means of misaligning the vertex segments with respect to the peripheral segments of the fingers 201 and respectively of misaligning the vertex and peripheral parts of the conical structure 202 under the effect of the axial stress as described hereinabove. As is also evident from FIG. 7, which is a view of the reinforcing element 200 from above when under axial stress, in this position, the tie 205 between each of the fingers 201 is under tension.

As will become evident from the description which follows, the natural abdominal pressure is another example of a situation that creates the axial stress as illustrated hereinabove on the reinforcing element, once it has been implanted.

Figure 8:
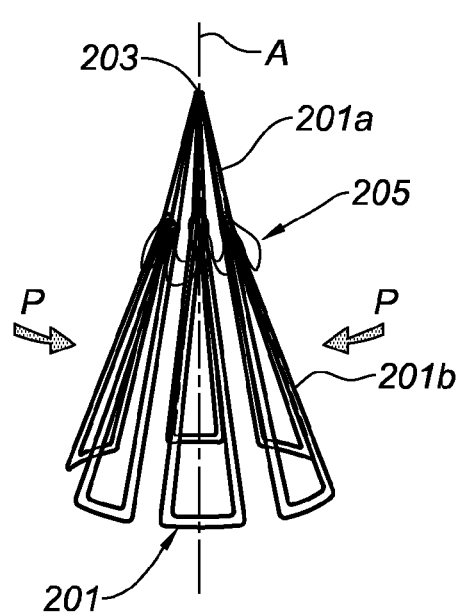
FIG. 8 is a side view of the reinforcing element of FIGS. 3 and 4 under centripetal radial stress.

With reference to FIG. 8, the reinforcing element 200 may also adopt a substantially cylindrical configuration under the effect of a stress known as a centripetal radial stress. Thus, if a pressure embodied by the arrow P in FIG. 8 is applied to the peripheral segments 201b of the fingers 201 in the centripetal radial direction, that is to say towards the central axis A of the conical structure 202 that passes through the vertex 203 of the said structure, the conical structure 202 is able to close up, that is to say to fold in on itself to adopt a substantially cylindrical configuration in which it occupies a small volume, by comparison with the positions of the reinforcing element 200 at rest or under axial stress. In such a configuration, as can be seen from FIG. 8, the tie 205 is very loose and forms loops between each of the fingers, the distance between the openings 201c being much shorter than the length of tie 205 between each opening 201c.

Figure 9:
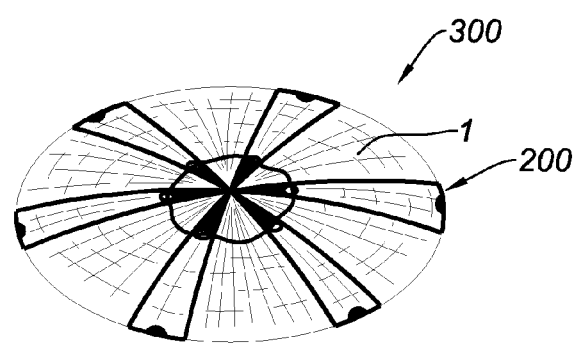
FIG. 9 is a perspective view of one embodiment of the prosthesis according to the invention.
Figure 10A:
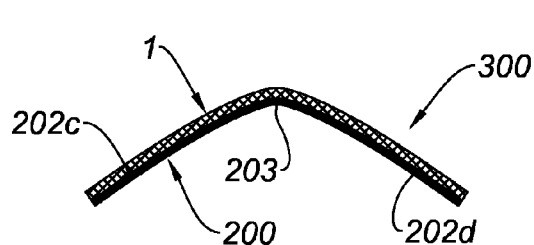
FIGS. 10a and 10b are cross sections through two embodiments of the prosthesis according to the invention.
Figure 10B:
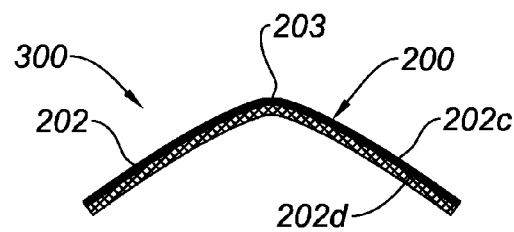

The reinforcing element 200 is intended to be associated with an implantable mesh 1 like the one depicted in FIG. 5. For that, the mesh 1 is fixed to the reinforcing element 200 in such a way as to hug the surface of the conical structure 202, as shown in FIG. 9. The mesh 1 can be fixed to the external surface 202c or, indifferently, to the internal surface 202d of the conical structure 202. FIG. 10a illustrates an embodiment in which the mesh 1 is fixed to the external surface 202c of the conical structure 202 of the reinforcing element 200. FIG. 10b illustrates an embodiment in which the mesh 1 is fixed to the internal surface 202d of the conical structure 202 of the reinforcing element 200.

This then yields a prosthesis 300 comprising the mesh 1 and the reinforcing element 200, the vertex 203 of the said conical structure 202 being positioned at the centre of the said mesh 1 and the said mesh 1 substantially hugging the internal 202d or external 202c surface of the said conical structure 202.

The reinforcing element 200 may be fixed to the mesh 1 by any method that provides reliable attachment of the mesh 1 and of the reinforcing element 200. For example, the reinforcing element 200 may be bonded, welded, for example using ultrasonic welding, thermobonded or stitched to the mesh 1. The reinforcing element 200 may be trapped within the arrangement of filaments that make up the mesh 1. In the prosthesis 300 thus obtained, in the embodiments described in FIGS. 9 to 10b, the tie 205 is flexible.

The mesh 1 is preferably cut to the dimensions of the reinforcing element so that the free ends of the fingers 201 adjoin the edges of the mesh, as shown in FIG. 9. As will become evident later on, it is preferable for the edges of the mesh 1 not to protrude beyond the free ends of the fingers over too great a distance.

Figure 11A:
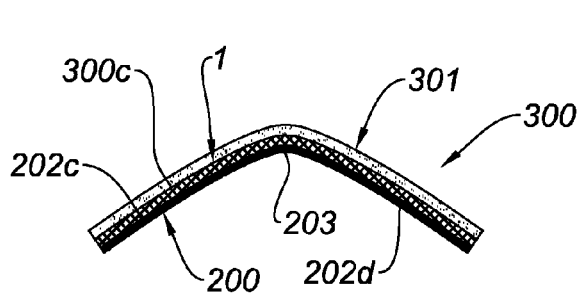
FIGS. 11a and 11b are cross sections through the two embodiments of FIGS. 10a and 10b, in which the prosthesis is covered with a non-stick coating.
Figure 11B:
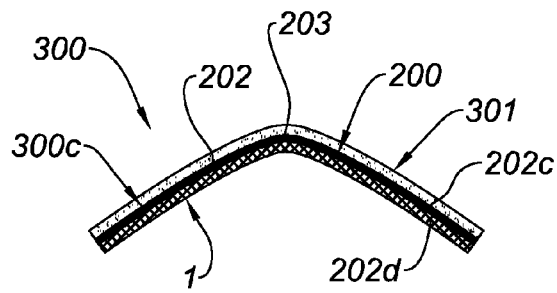

The prosthesis 300 may be covered with a non-stick coating on its external surface 300c so as in particular to avoid the formation of undesired post-surgery severe fibrous adhesions. Specifically, as will become evident from FIGS. 13-15 that follow, the external surface 300c of the prosthesis is the one intended to face the abdominal cavity 109 once the prosthesis 300 has been implanted. FIGS. 11a and 11b respectively illustrate the prostheses 300 of FIGS. 10a and 10b equipped with such a non-stick coating 301.

The non-stick material or coating is chosen from bioresorbable materials, non-bioresorbable materials and mixtures thereof. Non-bioresorbable non-stick materials may be chosen from polytetrafluoroethylene, polyethylene glycols, polysiloxanes, polyurethanes, stainless steels, derivatives of precious metals and mixtures thereof.

By preference, the said non-stick material or coating is bioresorbable: bioresorbable materials suitable for the said non-stick coating may be chosen from collagens, oxidized celluloses, polyacrylates, trimethylene carbonates, caprolactones, dioxanones, glycolic acid, lactic acid, glycolides, lactides, polysaccharides, for example chitosans, polyglucuronic acids, hyaluronic acids, dextranes and mixtures thereof.

The non-stick coating protects the mesh 1 of the prosthesis 300, at least during the initial phase of healing, namely protects the mesh 1 from exposure to inflammatory cells such as granulocytes, monocytes, macrophages or even multinuclear giant cells generally activated by the act of surgery. Specifically, at least during the initial healing phase, the duration of which may vary between 5 and 10 days approximately, only the non-stick coating is accessible to the various factors such as proteins, enzymes, cytokines or cells in the inflammatory line, at the first part of the textile.

When the non-stick coating is made up of non-resorbable materials, it thus protects the mesh 1 before and after implantation, throughout the implantation life of the prosthesis 300.

Moreover, thanks to the non-stick coating, the fragile surrounding tissue such as the hollow viscera, for example, are protected, particularly from the formation of undesired post-surgery severe fibrous adhesions.

When the non-stick material contains a bioresorbable material, it is preferable to choose a bioresorbable material that is not resorbed for a few days, so that the non-stick coating can perform its function of protecting the intestine and the hollow organs during the few days post-operation and do so until cell rehabilitation of the prosthesis in its turn can protect the fragile organs.

By preference, the non-stick coating may be applied to the external surface 300c of the prosthesis 300 by pouring a solution of non-stick material followed by gellification, as described in WO99/06080.

Figure 12:
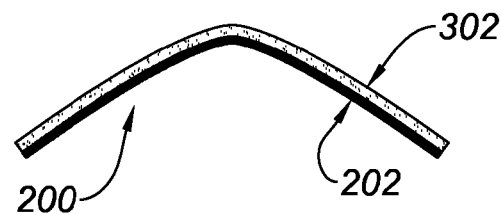
FIG. 12 is a cross section through another embodiment of the reinforcing element according to the invention.

In one embodiment of the invention, the non-stick coating is in the form of an initially independent film 302 which is combined with the reinforcing element 200 before the mesh 1 is fixed to the reinforcing element 200, as illustrated in FIG. 12. In such an embodiment, the film 302 is fixed to the external surface 202c of the conical structure 202 of the reinforcing element 200. The film 302 may, for example, be obtained by extrusion. The reinforcing element 200 may then be fixed to the said film 302 for example by bonding, thermal welding or alternatively by ultrasonic welding. Alternatively, the reinforcing element 200 is applied to a solution of non-stick material poured into a support: the reinforcing element is then trapped within the said film as the solution gels.

In all the embodiments described hereinabove, the mesh 1 and the non-stick coating (301, 302), whether or not the latter is in the form of an independent film, are flexible enough to accompany the successive deformations of the conical structure 202 of the reinforcing element 200 when the latter switches from its rest configuration to its configuration of FIG. 6 under axial stress or its configuration of FIG. 8 under centripetal radial stress. The tie 205 may potentially be trapped within the mesh 1 and/or the non-stick coating (301, 302) provided that it maintains its ability to switch from a flexible configuration when the reinforcing element 200 is in the rest position to a taut configuration when the reinforcing element 200 is under axial stress.

Furthermore, the mesh 1 and the non-stick coating, if present, perfectly espouse the shape of the conical structure 202: the reinforcing element 200 and its conical structure 202 reinforce the mesh 1; they act as a framework for the prosthesis 300, the mesh 1 connecting the various fingers 201 together. The non-stick coating may protrude slightly beyond the edges of the mesh 1.

Thus, the prosthesis 300, whether or not it is covered with the non-stick coating (301, 302), at rest has a conical configuration similar to that of the reinforcing element 200 and is also able to adopt a semi-planar and semi-conical configuration, under the effect of an axial stress applied to the said reinforcing element 200, and a cylindrical configuration under the effect of a centripetal radial stress applied to the peripheral segments of the fingers 201 of the reinforcing element 200.

Thus, when the reinforcing element 200 is in the configuration under axial stress, the vertex part of the mesh 1 maintains a conical shape whereas the peripheral part of the mesh 1 follows the spreading out of the peripheral segments 201b of the fingers 201 that form the conical structure 202 and adopts a planar configuration.

By way of example, the way in which the prosthesis 300 of FIG. 11a is fitted will now be described. It goes without saying that the fitting method described hereinbelow would apply in the same way to the prostheses of FIG. 10a, 10b or 11b and/or to prostheses comprising a mesh reinforced by the reinforcing elements of the invention as described in FIGS. 16 to 18b.

Figure 13:
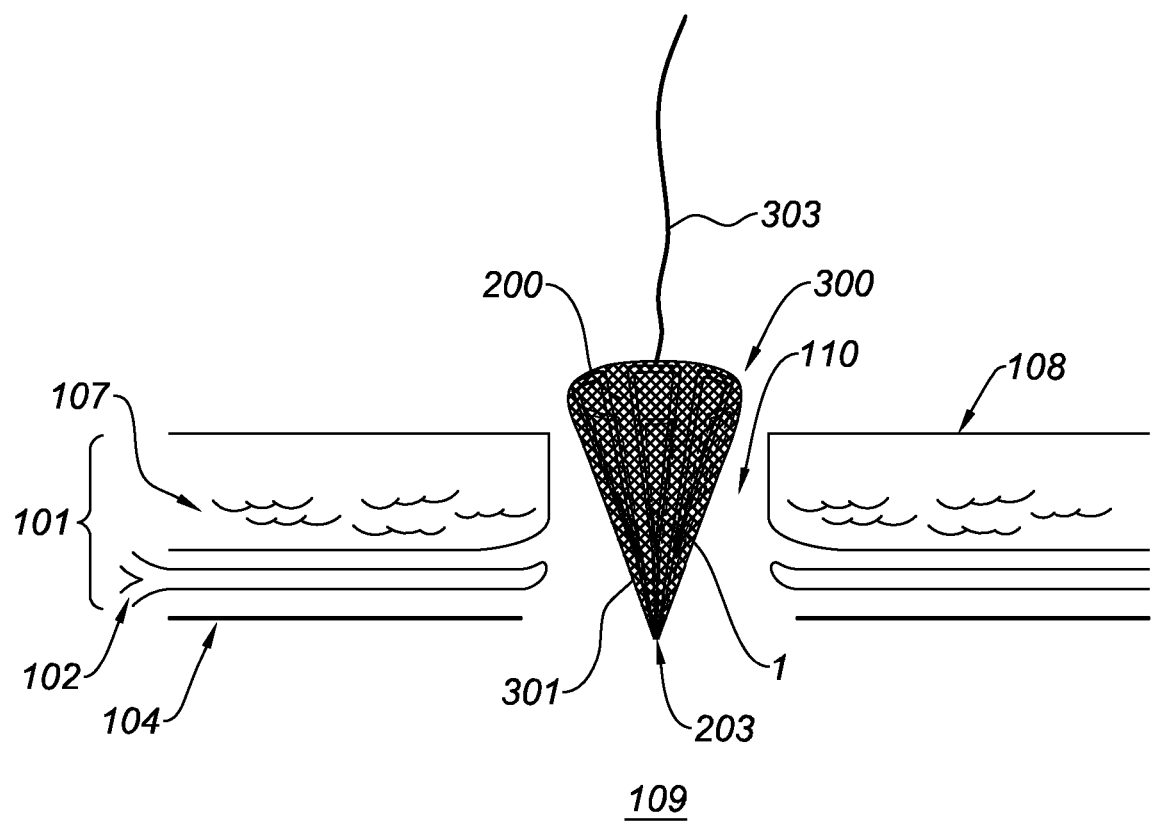
FIGS. 13 to 15 illustrate the various steps in the fitting of a prosthesis according to the invention to treat a hernia.

The prosthesis 300 is supplied to the surgeon in its rest configuration as depicted in FIG. 11 a. The prosthesis may already be equipped with a centering filament 303 fixed to the vertex 203 of the conical structure 202 of the reinforcing element 200 and extending towards the inside of the prosthesis 300, the length of this centering filament 303 far exceeding the length of the prosthesis 300 in its cylindrical configuration. Alternatively, the prosthesis 300 may be supplied without a centering filament and the surgeon then installs such a filament before introducing the prosthesis 300 into the implantation site. The surgeon may also make use of a number of centering filaments Having made the incision 110 described in FIG. 2, the surgeon applies a centripetal radial stress to the prosthesis 300 as described hereinabove using his fingers so as to bring the prosthesis 300 into a substantially cylindrical configuration as shown in FIG. 13. The prosthesis 300 thus occupies a particularly limited volume allowing it to be introduced easily through the incision 110. As shown in FIG. 13, the prosthesis 300 is introduced into the abdominal cavity 109, with the vertex 203 of the conical structure 202 facing towards the abdominal cavity 109. In this figure, for reasons of clarity, the fingers of the surgeon holding, on the one hand, the prosthesis 300 in its cylindrical configuration and, on the other hand, the free end of the centering filament 303, have not been depicted.

Figure 14:
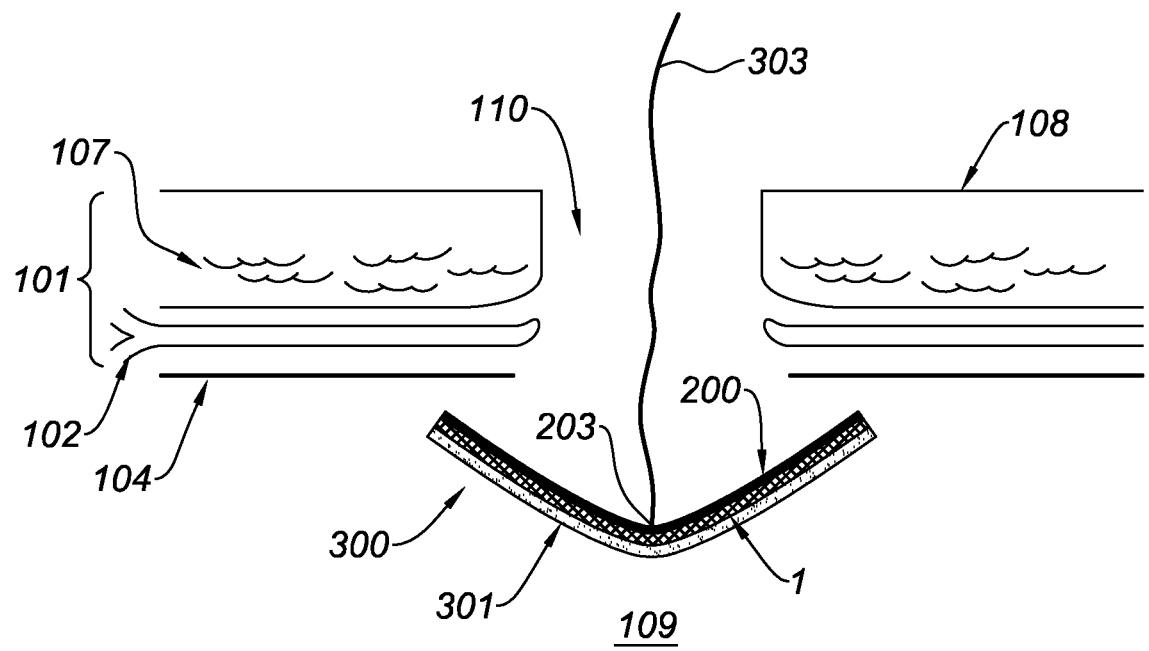

Once the prosthesis 300 is in the abdominal cavity 109, the surgeon relaxes the centripetal radial pressure he was exerting thereon. Because of its elasticity, the reinforcing element 200, and therefore the prosthesis 300, reverts to its rest configuration as described in FIGS. 4 and 11a. Thus, as shown in FIG. 14, the prosthesis 300 deploys automatically into the abdominal cavity 109, with its external face, the one covered with the non-stick coating 301, facing towards the abdominal cavity 109.

Figure 15:
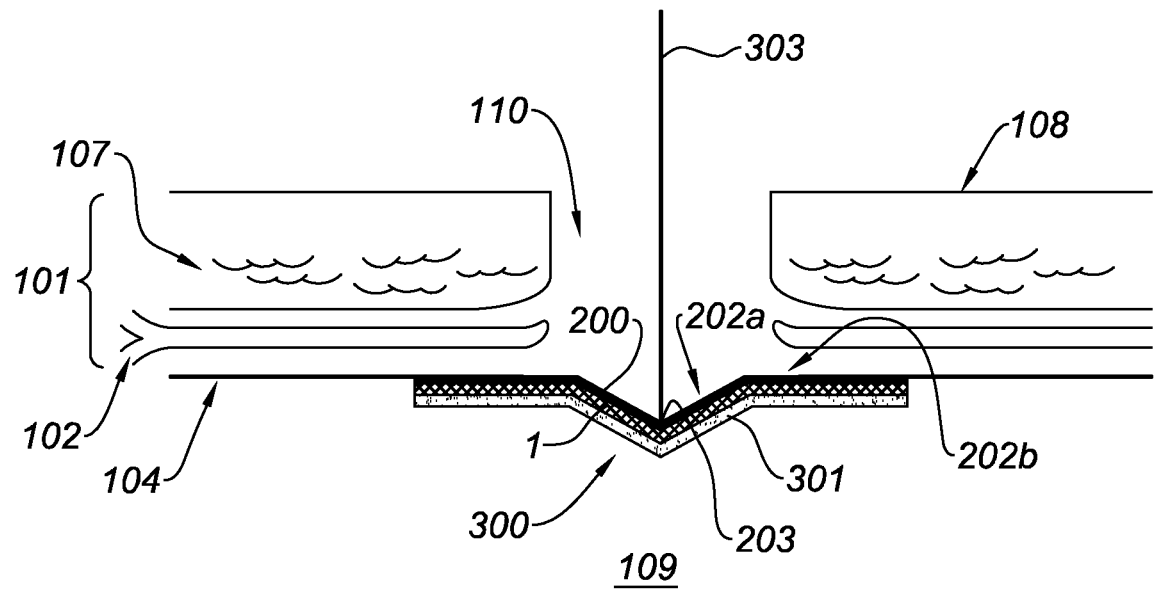

In a next step, the surgeon uses the centering filament 303 both to center the prosthesis 300 with respect to the incision 110 and to press the prosthesis 300 firmly against the abdominal wall (101, 104). To do this, he pulls significantly on the centering filament 303. During this step, the surgeon may pull on the centering filament 303 without having to fear risking a reversion of the prosthesis 300. Quite the contrary; in the situation described in FIG. 15, the pulling force that the surgeon applies to the centering filament 303 is equivalent to the pressure applied to the vertex 203 of the conical structure 202 of the reinforcing element 200 with reference to FIG. 6. Thus, the more firmly the surgeon pulls on the centering filament 303 placing the latter under tension, the more the peripheral part 202 b of the conical structure 202 of the reinforcing element 200, and therefore of the prosthesis 300, spreads out and is pressed firmly against the abdominal wall (101, 104), espousing the shape thereof whereas, on the other hand, the vertex part 202 a of the conical structure 202 of the reinforcing element 200, and therefore of the prosthesis 300, maintains a conical shape, as shown in FIG. 15, thus preventing any possible reversion of the reinforcing element 200, and therefore of the prosthesis 300 which is firmly connected thereto.

During this step, the fact that the peripheral segments are of a shape that widens towards the free ends 204 of the fingers 201 of the reinforcing element 200 of the prosthesis 300 allows the prosthesis 300 to be pressed optimally against the surface and avoids soft organs becoming trapped between the prosthesis 300 and the abdominal wall (101, 104). Thus, the greater the proportion of the periphery of the mesh 1 occupied by the contours of the peripheral segments 201b at the free ends 204 of the fingers 201, the more firmly the prosthesis 300 will be pressed against the surface. In addition, the fact that the edges of the mesh 1 preferably do not protrude beyond the fingers 201 makes it possible to prevent the prosthesis 300 from forming creases or viscera from becoming trapped between the mesh 1 and the abdominal wall (101, 104). Moreover, the relative independence of the fingers 201 of the reinforcing element 200, which are linked together essentially at the vertex part of the conical structure, gives the reinforcing element 200 a degree of flexibility and allows each finger 201 to adapt to suit any potential local deformation of the abdominal wall (101, 104), whether this deformation be a natural deformation or one caused by a movement of the patient, while at the same time keeping the prosthesis 300 pressed firmly against this wall (101, 104).

All that then remains for the surgeon to do is to suture the centering filament 303 to the abdominal wall (101, 104), closing up the incision 110. As can be seen in FIG. 15, the prosthesis 300 is thus perfectly deployed, spread out and pressed firmly against the abdominal wall (101, 104) without the risk of any viscera becoming trapped between the prosthesis and the abdominal wall (101, 104). When the prosthesis 300 is in this implanted position, the vertex part and the peripheral part of the prosthesis 300 are not aligned: specifically, the natural abdominal pressure creates the axial stress situation described in FIG. 6 and keeps the reinforcing element 200 under axial stress for the duration of the time that the said reinforcing element 200 is present in the patient's body. If the reinforcing element 200 is a bioresorbable one, the resorption time is chosen to be long enough that the mesh 1 has a chance to be recolonized before the reinforcing element 200 disappears. Fixation of the mesh 1 is thus assured over the long term.

The prosthesis according to the invention is particularly simple to fit. This fitting is also particularly reliable, any risk of the trapping of viscera and any risk of reversion of the prosthesis being avoided. A prosthesis according to the invention, equipped with a reinforcing element according to the invention, is particularly well suited to the treatment of umbilical hernias for which the abdominal incision made is of small size. Specifically, the prosthesis according to the invention, equipped with the reinforcing element according to the invention, is able to adopt a substantially cylindrical configuration occupying a particularly small volume that allows it to be inserted easily into the abdominal cavity via a small-sized incision and without requiring the use of a special ancillary tool. Thanks to its special structure, the prosthesis according to the invention deploys automatically in the abdominal cavity without the intervention of an additional tool. Again thanks to its special structure, the prosthesis according to the invention can be spread out and pressed firmly against the abdominal wall effectively, once again without requiring the intervention of a special tool to assist with spreading out. The prosthesis according to the invention thus allows effective, simple and rapid treatment of a hernia, particularly an umbilical hernia, minimizing the risks of a relapse.

FIGS. 16 to 18b depict other embodiments of the reinforcing element according to the invention.

Figure 16:
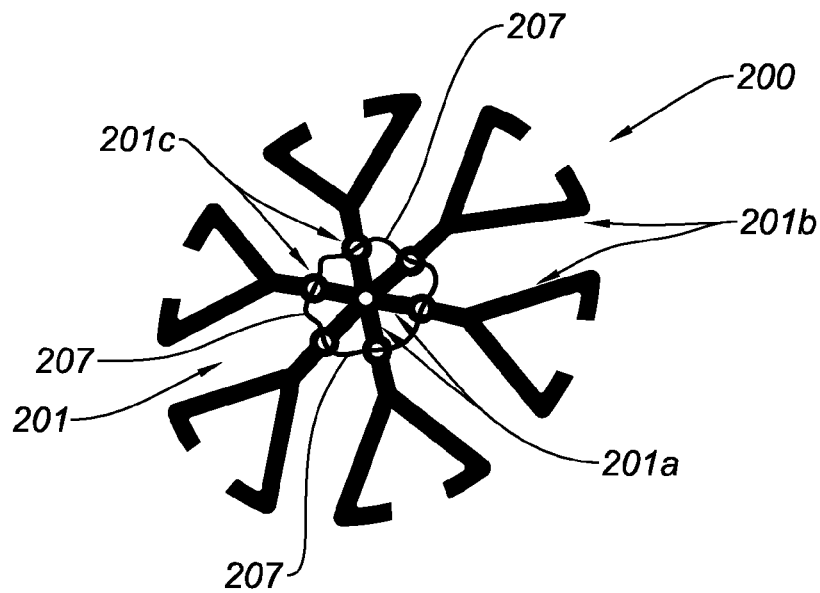
FIG. 16 is a perspective view of another embodiment of a reinforcing element according to the invention.

FIG. 16 is a perspective depiction of an alternative form of the reinforcing element 200 described in FIGS. 1 to 15. Those references that denote the same elements have been retained. The reinforcing element 200 in FIG. 16 differs from that of FIG. 3 in that the peripheral segments 201b of the fingers 201 form triangles which are open at the free ends of the fingers 201 and in that the tie is replaced by a plurality of flexible bridges 207 of material, each bridge of material connecting a finger 201 to an adjacent finger 201. The bridges of material 207 may, for example, be formed of the same material as the reinforcing element and moulded therewith at the time of its manufacture. The bridges of material 207 are flexible enough that they can pass from a flexible or loose configuration, when the reinforcing element is in the rest position, to a taut or tensioned configuration in the position in which the reinforcing element 200 is under axial stress. Like the reinforcing element in FIG. 3, the fingers 201 of the reinforcing element of FIG. 16 are flexible and elastic and are able to deform, under the action of an axial stress and with the bridges of material 207 becoming tensioned, so that the peripheral segments 201b are no longer aligned with the vertex segments 201a, the effect of this being that the peripheral part of the conical structure formed by the fingers 201 flattens, espousing the shape of a planar surface, whereas its vertex part maintains its conical shape.

It goes without saying that the bridges of material 207 described hereinabove could replace the tie 205 described for the embodiment of the reinforcing element 200 of FIGS. 1-15. Likewise, the perforated palm-shaped peripheral segments of the reinforcing element of FIGS. 1-15 could be replaced by the open triangles described with reference to FIG. 16.

Figure 17A:
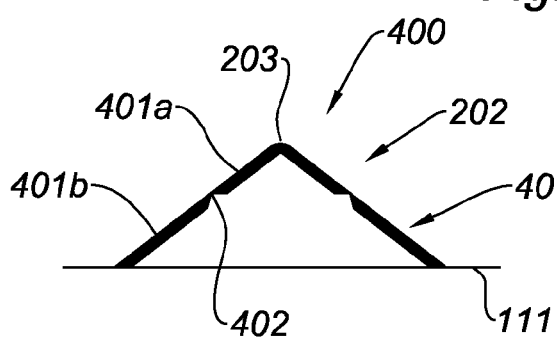
FIGS. 17a and 17b are schematic cross sections, at rest and under axial stress, respectively, of another embodiment of a reinforcing element according to the invention.
Figure 17B:
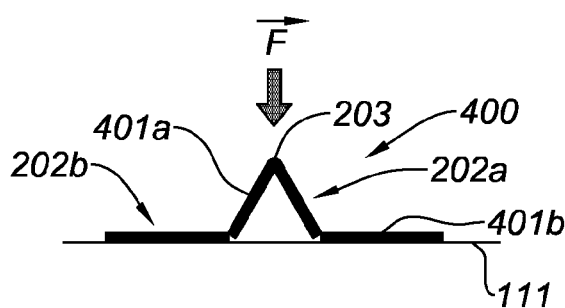

FIGS. 17a and 17b are schematic depictions of another embodiment of a reinforcing element 400 according to the invention, at rest and under axial stress respectively, and in which the misalignment means are formed, for each finger 401, by a deficiency of material 402, created at the junction between the vertex segment 401a and the peripheral segment 401b, on the internal surface of the conical structure 202. In such an embodiment, the pressure applied under axial stress to the vertex 203 of the conical structure causes, because of the deficiency of material 402, the peripheral segments 401b to flex or buckle as shown in FIG. 17b, being then no longer aligned with the vertex segments 401a. As shown in FIG. 17b, the peripheral part 202b of the conical structure adopts a planar configuration whereas the vertex part 202a maintains a conical shape.

Figure 18A:
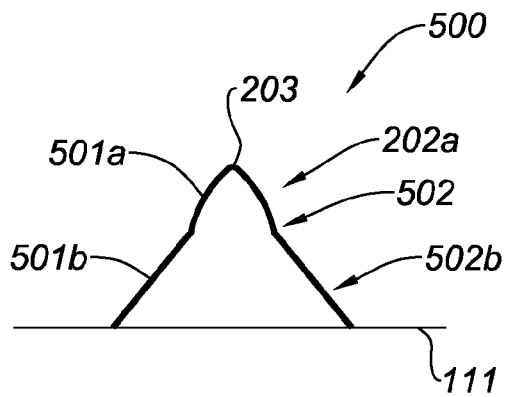
FIGS. 18a and 18b are schematic cross sections, at rest and under axial stress, respectively, of another embodiment of a reinforcing element according to the invention.
Figure 18B:
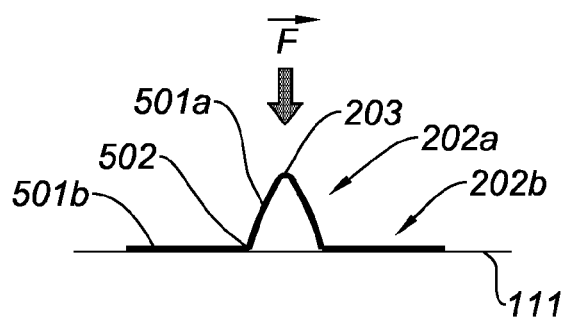

FIGS. 18a and 18b are schematic depictions of another embodiment of a reinforcing element 500 according to the invention, at rest and under axial stress respectively, and in which the misalignment means are formed, for each finger 501, by an elbow 502, situated at the junction between the vertex segment 501a and the peripheral segment 501b, the vertex segment having a slightly rounded shape giving the vertex part of the conical structure 202a a sugarloaf shape. In such an embodiment, for each finger 501, the vertex segment 501a and the peripheral segment 501b are, when the reinforcing element 500 is in the rest position, slightly misaligned, the peripheral segment having a rectilinear profile. Thus, the peripheral segments 501b define an axisymmetric cone frustum. Moreover, in this embodiment, for each finger, the said vertex segment and the said peripheral segment are joined together and consist of a single elastic tab. The pressure applied under axial stress to the vertex 203 of the conical structure, because of the presence of the elbow 502 and because of the rounded shape of the vertex segment 501a, causes the peripheral segment 501b to flex or buckle with respect to the vertex segment 501a, as shown in FIG. 18b, thus accentuating the misalignment of one segment with respect to the other. As shown in FIG. 18b, the peripheral part 202b of the conical structure adopts a planar configuration whereas the vertex part 202a maintains a substantially conical sugarloaf shape.

What is claimed is:

1. An implantable reinforcing element, comprising:
   a plurality of fingers extending outwardly from a central point defining a vertex of the implantable reinforcing element configured to form a substantially conical structure when the reinforcing element is in a rest configuration, each finger comprising a vertex segment and a peripheral segment, a collection of the vertex segments of the fingers defining a vertex part of the substantially conical structure and a collection of the peripheral segments of the fingers defining a peripheral part of the substantially conical structure,
   a collection of free ends of the plurality of fingers positioned at an opposite end from the central point which form a base of the substantially conical structure, the plurality of fingers being fixed freely to the central point and configured to allow the substantially conical structure to open out when the base of the conical structure is brought into contact with a substantially planar surface and a pressure force is applied to the reinforcing element from the central point of the substantially conical structure towards the base,
   a misalignment tie passing through an opening of each of the fingers and configured to misalign the vertex segment and the peripheral segment of each finger,
   wherein when the reinforcing element is in a position of axial stress the misalignment tie provides for the peripheral part of the conical structure to adopt a substantially planar configuration and to hug the substantially planar surface, and for the vertex part of the structure to maintain a substantially conical shape.

2. The reinforcing element according to claim 1, wherein at least part of the misalignment tie is situated at a junction between the vertex segment and the peripheral segment.

3. The reinforcing element according to claim 1, wherein the reinforcing element is configured to adopt a substantially cylindrical configuration under radial and centripetal stress when configuration pressure is applied to the peripheral segments in a radial and centripetal direction.

4. The reinforcing element according to claim 1, wherein each peripheral segment has a shape that widens towards the free end of the finger and wherein each vertex segment tapers towards the central point.

5. The reinforcing element according to claim 4, wherein at least one peripheral segment is perforated.

6. The reinforcing element according to claim 4, wherein all the peripheral segments are perforated.

7. The reinforcing element according to claim 1, wherein, for each finger, the vertex segment and the peripheral segment are joined together and consist of a single elastic tab.

8. The reinforcing element according to claim 7, wherein the misalignment tie is tension-free when the reinforcing element is in the rest configuration, the misalignment tie is under tension when the reinforcing element is under axial stress.

9. The reinforcing element according to claim 7, wherein the vertex segment and the peripheral segment are slightly misaligned when the reinforcing element is in the rest configuration.

10. The reinforcing element according to claim 9, wherein the vertex segments define a conical sugarloaf shape of the vertex part of the substantially conical structure, the peripheral segments defining an axisymmetric cone frustum.

11. The reinforcing element according to claim 1, wherein the misalignment tie includes a material deficiency created on an internal surface of the substantially conical structure, at the junction between the vertex segment and the peripheral segment of each finger.

12. The reinforcing element according to claim 1, wherein a non-stick film is fixed to an external surface of the substantially conical structure of the reinforcing element.

13. The reinforcing element according to claim 1, wherein a centering filament is fixed to the central point of the substantially conical structure.

14. A prosthesis comprising an implantable mesh, wherein a reinforcing element according to claim 1 is fixed to the mesh, the central point of the substantially conical structure being positioned at a center of the mesh and the mesh substantially hugging the surface of the substantially conical structure.

15. The prosthesis according to claim 14, wherein edges of the mesh adjoin the free ends of the fingers of the reinforcing element.

16. The prosthesis according to claim 14, further comprising a non-stick coating on an external surface of the prosthesis.

* * * * *